US008246642B2

(12) United States Patent
Houser et al.

(10) Patent No.: US 8,246,642 B2
(45) Date of Patent: Aug. 21, 2012

(54) ULTRASONIC MEDICAL INSTRUMENT AND MEDICAL INSTRUMENT CONNECTION ASSEMBLY

(75) Inventors: Kevin L. Houser, Springboro, OH (US); Lee E. Reichel, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1215 days.

(21) Appl. No.: 11/291,174

(22) Filed: Dec. 1, 2005

(65) Prior Publication Data

US 2007/0129723 A1    Jun. 7, 2007

(51) Int. Cl.
*A61B 17/32* (2006.01)
(52) U.S. Cl. ........................................................ 606/169
(58) Field of Classification Search .................. 606/169, 606/1, 40, 45, 47, 170; 600/459, 461
See application file for complete search history.

(56) References Cited

U.S. PATENT DOCUMENTS

| 4,452,473 A | * | 6/1984 | Ruschke .......................... 285/81 |
| 4,660,573 A | * | 4/1987 | Brumbach ...................... 606/128 |
| 4,696,667 A | | 9/1987 | Masch |
| 4,979,952 A | * | 12/1990 | Kubota et al. ................. 606/169 |
| 5,057,119 A | * | 10/1991 | Clark et al. .................... 606/169 |
| 5,059,210 A | | 10/1991 | Clark et al. |
| 5,156,613 A | | 10/1992 | Sawyer |
| 5,167,725 A | | 12/1992 | Clark et al. |
| 5,205,817 A | | 4/1993 | Idemoto et al. |
| 5,209,776 A | | 5/1993 | Bass et al. |
| 5,242,385 A | * | 9/1993 | Strukel ........................... 604/22 |
| 5,261,922 A | | 11/1993 | Hood |
| 5,263,957 A | | 11/1993 | Davison |
| 5,289,436 A | | 2/1994 | Terhune |
| 5,306,280 A | | 4/1994 | Bregen et al. |
| 5,318,570 A | * | 6/1994 | Hood et al. ...................... 606/99 |
| 5,322,055 A | | 6/1994 | Davison et al. |
| 5,324,297 A | | 6/1994 | Hood et al. |
| 5,324,299 A | | 6/1994 | Davison et al. |
| 5,342,292 A | * | 8/1994 | Nita et al. ........................ 604/22 |

(Continued)

FOREIGN PATENT DOCUMENTS

EP    0695535    2/1996

(Continued)

OTHER PUBLICATIONS

LigaSure* Xtd, tyco Healthcare, Valleylab (Nov. 2002).

*Primary Examiner* — S. Thomas Hughes
*Assistant Examiner* — Sarah Simpson
(74) *Attorney, Agent, or Firm* — Thompson Hine L.L.P.

(57) ABSTRACT

An ultrasonic medical instrument having a handpiece and medical ultrasonic blade assembly including a vibration antinode, a handpiece, and a medical ultrasonic blade. The blade is threadably engaged by the handpiece proximate the vibration antinode. The blade is in ultrasound-transmitting physical contact with the handpiece proximate the vibration antinode and apart from where the medical ultrasonic blade is threadably engaged by the handpiece. A medical-instrument connection assembly for transmitting ultrasonic vibrations includes first, second, and third connecting members. The first connecting member is adapted to be ultrasonically vibrated and has a longitudinal axis. The second connecting member is capable of being positioned to be substantially coaxially aligned with the longitudinal axis and in ultrasound-transmitting physical contact with the first connecting member. The third connecting member surrounds, and is rotatably or fixedly attached to, the second connecting member and is threadably engageable with the first connecting member.

12 Claims, 2 Drawing Sheets

U.S. PATENT DOCUMENTS

| | | | |
|---|---|---|---|
| 5,372,585 | A | 12/1994 | Tiefenbrun et al. |
| 5,383,883 | A | 1/1995 | Wilk et al. |
| 5,647,851 | A | 7/1997 | Pokras |
| 5,735,875 | A | 4/1998 | Bonutti et al. |
| 5,807,310 | A * | 9/1998 | Hood ............... 604/22 |
| 5,810,869 | A * | 9/1998 | Kaplan et al. ............... 606/194 |
| 5,836,897 | A | 11/1998 | Sakurai et al. |
| 5,843,109 | A * | 12/1998 | Mehta et al. ............... 606/169 |
| 5,853,290 | A | 12/1998 | Winston |
| 5,893,880 | A | 4/1999 | Egan et al. |
| 5,895,412 | A | 4/1999 | Tucker |
| 5,910,150 | A | 6/1999 | Saadat |
| 5,935,143 | A * | 8/1999 | Hood ............... 606/169 |
| 5,941,887 | A * | 8/1999 | Steen et al. ............... 606/107 |
| 5,957,943 | A | 9/1999 | Vaitekunas |
| 5,989,275 | A | 11/1999 | Estabrook et al. |
| 6,004,335 | A | 12/1999 | Vaitekunas et al. |
| 6,033,375 | A * | 3/2000 | Brumbach ............... 604/22 |
| 6,051,010 | A | 4/2000 | DiMatteo et al. |
| 6,053,906 | A | 4/2000 | Honda et al. |
| 6,063,098 | A | 5/2000 | Houser et al. |
| 6,206,877 | B1 | 3/2001 | Kese et al. |
| 6,217,591 | B1 | 4/2001 | Egan et al. |
| 6,270,471 | B1 * | 8/2001 | Hechel et al. ............... 604/22 |
| 6,283,981 | B1 | 9/2001 | Beaupre |
| 6,325,811 | B1 | 12/2001 | Messerly |
| 6,352,532 | B1 | 3/2002 | Kramer et al. |
| 6,409,743 | B1 | 6/2002 | Fenton, Jr. |
| 6,436,114 | B1 | 8/2002 | Novak et al. |
| 6,458,142 | B1 | 10/2002 | Faller et al. |
| 6,491,708 | B2 * | 12/2002 | Madan et al. ............... 606/169 |
| 6,526,976 | B1 | 3/2003 | Baran |
| 6,561,983 | B2 * | 5/2003 | Cronin et al. ............... 600/461 |
| 6,562,059 | B2 | 5/2003 | Edwards et al. |
| 6,616,450 | B2 | 9/2003 | Mossle et al. |
| 6,623,444 | B2 * | 9/2003 | Babaev ............... 604/22 |
| 6,689,086 | B1 | 2/2004 | Nita et al. |
| 6,695,782 | B2 * | 2/2004 | Ranucci et al. ............... 600/439 |
| 6,699,214 | B2 | 3/2004 | Gellman |
| 6,702,761 | B1 | 3/2004 | Damadian et al. |
| 6,887,221 | B1 * | 5/2005 | Baillargeon et al. ............ 604/181 |
| 6,887,252 | B1 | 5/2005 | Okada et al. |
| 6,908,466 | B1 | 6/2005 | Bonutti et al. |
| 7,018,354 | B2 * | 3/2006 | Tazi ............... 604/22 |
| 7,335,997 | B2 | 2/2008 | Wiener |
| 7,338,463 | B2 | 3/2008 | Vigil |
| 2001/0025184 | A1 | 9/2001 | Messerly |
| 2002/0045860 | A1 | 4/2002 | Sussman et al. |
| 2002/0103438 | A1 * | 8/2002 | Cronin et al. ............... 600/459 |
| 2002/0138037 | A1 | 9/2002 | Weimann |
| 2002/0193798 | A1 * | 12/2002 | Oh et al. ............... 606/80 |
| 2004/0006347 | A1 | 1/2004 | Sproul |
| 2004/0039242 | A1 | 2/2004 | Tolkoff et al. |
| 2004/0176686 | A1 | 9/2004 | Hare et al. |
| 2005/0004589 | A1 | 1/2005 | Okada et al. |
| 2005/0038340 | A1 | 2/2005 | Vaezy et al. |
| 2005/0049546 | A1 * | 3/2005 | Messerly et al. ............... 604/22 |
| 2005/0085728 | A1 | 4/2005 | Fukuda |
| 2005/0131401 | A1 | 6/2005 | Malecki et al. |
| 2005/0143726 | A1 | 6/2005 | Bortkiewicz |
| 2006/0257819 | A1 | 11/2006 | Johnson |
| 2007/0060926 | A1 * | 3/2007 | Escaf ............... 606/107 |
| 2007/0239028 | A1 | 10/2007 | Houser et al. |

FOREIGN PATENT DOCUMENTS

| | | |
|---|---|---|
| EP | 1108394 | 6/2001 |
| EP | 1543854 | 6/2005 |
| EP | 1707131 | 10/2006 |
| WO | 02/76685 | 10/2002 |
| WO | 03/002189 | 1/2003 |
| WO | WO 03/024513 | 3/2003 |
| WO | WO 2004/060447 | 7/2004 |
| WO | 2005/056104 | 6/2005 |
| WO | WO 2005/056104 | 6/2005 |
| WO | 2005/084251 | 9/2005 |

* cited by examiner

ULTRASONIC MEDICAL INSTRUMENT AND MEDICAL INSTRUMENT CONNECTION ASSEMBLY

FIELD OF THE INVENTION

The present invention is related generally to medical instruments, and more particularly to an ultrasonic medical instrument and to a medical-instrument connection assembly.

BACKGROUND OF THE INVENTION

Medical instruments are known which include a handpiece and a medical ultrasonic blade assembly. The handpiece contains an ultrasound transducer. The ultrasonic blade of the assembly makes physical contact with, and is connected to, the handpiece of the assembly only by a threaded connection (internal threads on the blade and external threads on the handpiece) proximate a vibration antinode. This requires multiple turns to attach the blade, requires a torque-limiting device to correctly attach the blade, and is prone to threads being stripped or broken. Quick connections are known which had the blade contact the handpiece at a vibration antinode but provided the force to hold the two members together at a vibration node. This did not work reliably over a wide range of inputs and was not implemented.

Still, scientists and engineers continue to seek improved handpiece and medical ultrasonic blade assemblies and improved medical-instrument connection assemblies.

SUMMARY OF THE INVENTION

A first expression of an embodiment of the invention is for an ultrasonic medical instrument having a handpiece and medical ultrasonic blade assembly. The handpiece and medical ultrasonic blade assembly includes a vibration antinode, a handpiece and a medical ultrasonic blade. The medical ultrasonic blade is threadably engaged by the handpiece proximate the vibration antinode. The medical ultrasonic blade is in ultrasound-transmitting physical contact with the handpiece proximate the vibration antinode and apart from where the medical ultrasonic blade is threadably engaged by the handpiece.

A second expression of an embodiment of the invention is for a medical-instrument connection assembly for transmitting ultrasonic vibrations and includes an ultrasound-medical-instrument first connecting member, an ultrasound-medical-instrument second connecting member, and an ultrasound-medical-instrument third connecting member. The first connecting member is adapted to be ultrasonically vibrated and has a longitudinal axis. The second connecting member is capable of being positioned to be substantially coaxially aligned with the longitudinal axis and in ultrasound-transmitting physical contact with the first connecting member. The third connecting member surrounds, and is rotatably or fixedly attached to, the second connecting member and is threadably engageable with the first connecting member.

Several benefits and advantages are obtained from one or more of the expressions of an embodiment of the invention. In one example, physical contact and threadable engagement (internal threads on the handpiece acting on the external diameter of the blade) proximate a longitudinal vibration antinode provide improved ultrasound transfer while threadable engagement radially apart from the physical contact allows for a quick connection (and disconnection) without requiring multiple turns or a torque limiting device while reducing the possibility of stripped or broken threads.

The present invention has, without limitation, application with straight or curved ultrasonic surgical blades and further in hand-activated instruments as well as in robotic-assisted instruments.

DETAILED DESCRIPTION OF THE INVENTION

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the convenience of the reader and are not for the purpose of limiting the invention.

It is understood that any one or more of the following-described embodiments, examples, etc. can be combined with any one or more of the other following-described embodiments, examples, etc.

Figure 1:
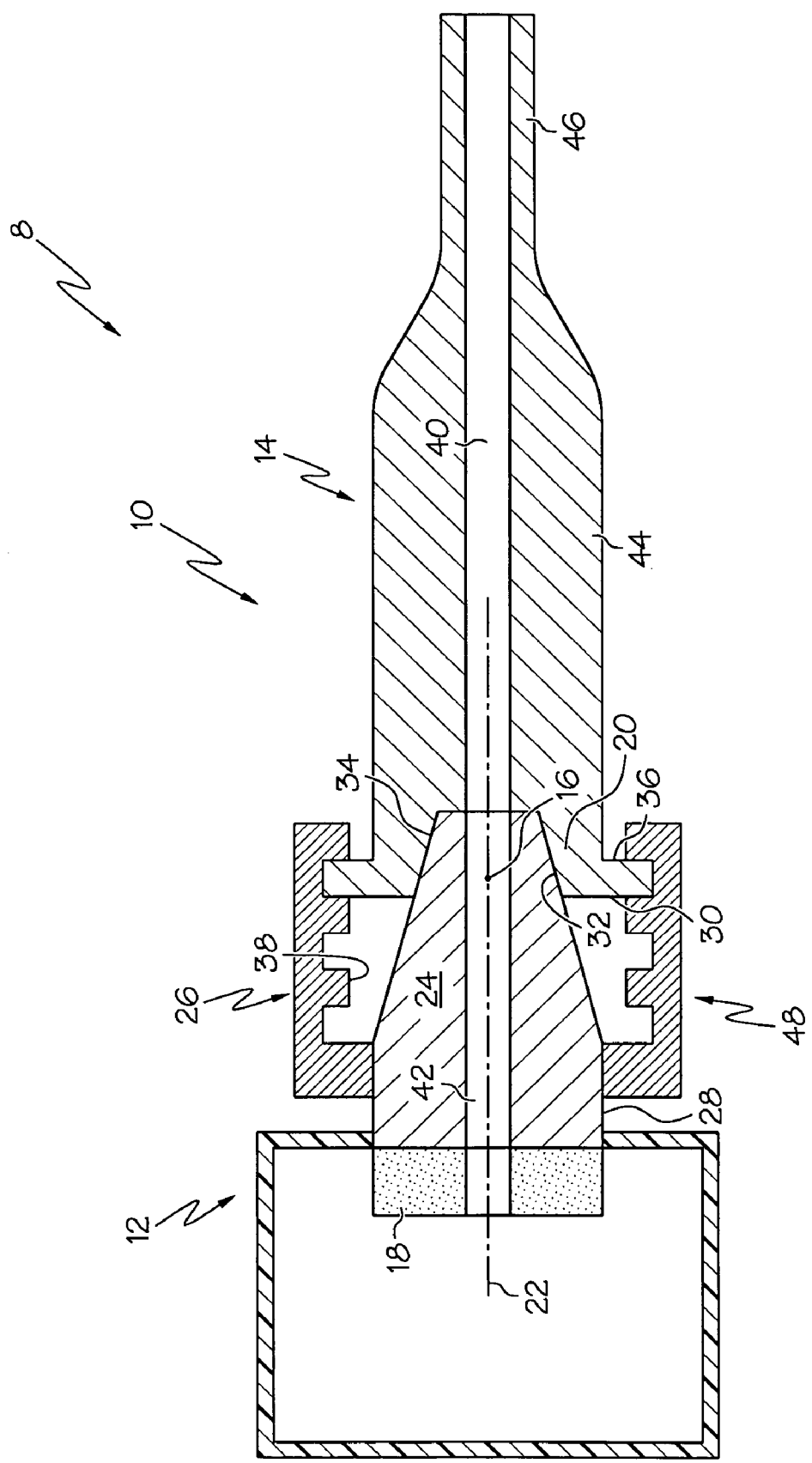
FIG. 1 is a schematic cross-sectional view of a first embodiment of an ultrasonic medical instrument of the invention, including an embodiment of a medical-instrument connection assembly of the invention, wherein the handpiece makes a tapered physical contact with the wave guide portion of the blade, and wherein the third connecting member is fixedly attached to the second connecting member.

Referring now to the Figures, in which like numerals indicate like elements, FIG. 1 illustrates a first embodiment of the invention. A first expression of the embodiment of FIG. 1 is for an ultrasonic medical instrument 8 having a handpiece and medical ultrasonic blade assembly 10. The handpiece and medical ultrasonic blade assembly 10 includes a vibration antinode 16, a handpiece 12, and a medical ultrasonic blade 14. The medical ultrasonic blade 14 is threadably engaged by the handpiece 12 proximate the vibration antinode 16. The medical ultrasonic blade 14 is in ultrasound-transmitting physical contact with the handpiece 12 proximate the vibration antinode 16 and apart from where the medical ultrasonic blade 14 is threadably engaged by the handpiece 12.

In one enablement of the first expression of the embodiment of FIG. 1, the handpiece 12 includes an ultrasound transducer 18, the vibration antinode 16 is a longitudinal vibration antinode, and the medical ultrasonic blade 14 is in ultrasound-transmitting physical contact with the handpiece 12 transversely apart (such as radially apart in the case of a circularly cylindrical blade) from where the medical ultrasonic blade 14 is threadably engaged by the handpiece 12. It is noted that the term "proximate" includes, without limitation, the word "at". Other enablements, including handpieces which transfer ultrasound vibration from an ultrasound transducer located remote from the handpiece, and including nonlongitudinal vibrational modes, are left to those skilled in the art. It is noted that electrical connections to the handpiece (such as a cable from a generator outside the handpiece to the ultrasound transmitter inside the handpiece) and fluid connections to the handpiece have been omitted from FIG. 1 for clarity.

In one arrangement of the first expression of the embodiment of FIG. 1, the medical ultrasonic blade 14 includes a first connecting member 20 having a longitudinal axis 22. In this arrangement, the handpiece 12 includes a second connecting member 24 which is substantially coaxially aligned with the longitudinal axis 22 and which is in ultrasound-transmitting physical contact with the first connecting member 20 proximate the vibration antinode 16. In this arrangement, the handpiece 12 includes a third connecting member 26 which surrounds, and is rotatably or fixedly attached to, the second connecting member 24 and which is threadably engaged with the first connecting member 20 proximate the vibration antinode 16.

In one construction of the first expression of the embodiment of FIG. 1 having the connecting-member arrangement, the first connecting member 20 is a monolithic portion of the medical ultrasonic blade 14. In one variation, the handpiece 12 includes an ultrasound transducer 18 and a protrusion 28 operatively connected to the ultrasound transducer 18. In one modification, the second connecting member 24 is a monolithic portion of the protrusion 28. In one example, the third connecting member 26 is fixedly attached to the second connecting member 24 by being a monolithic portion of the protrusion 28. Non-monolithic members and their attachments are left to the artisan.

In a first application of the first expression of the embodiment of FIG. 1 having the connecting-member arrangement, the first connecting member 20 includes a substantially longitudinally-facing surface 30 having a tapered recess 32, and the second connecting member 24 has a tapered end 34 engaged in the tapered recess 32. The taper of the tapered recess 32 is greater than the taper of the tapered end 34 to insure ultrasound-transmitting physical contact. In one variation, the first connecting member 20 has a substantially transversely-outwardly-extending annular wing 36, and the third connecting member 26 has internal threads 38 threadably engaging the annular wing 36. In one modification, the first connecting member 20 has a first lumen 40, and the second connecting member 24 has a second lumen 42 in fluid communication with the first lumen 40. In one employment, liquid is transmitted to patient tissue through the first and second lumens 40 and 42. In one example, the first, second and third connecting members 20, 24 and 26 together define a luer-type connection.

Figure 2:
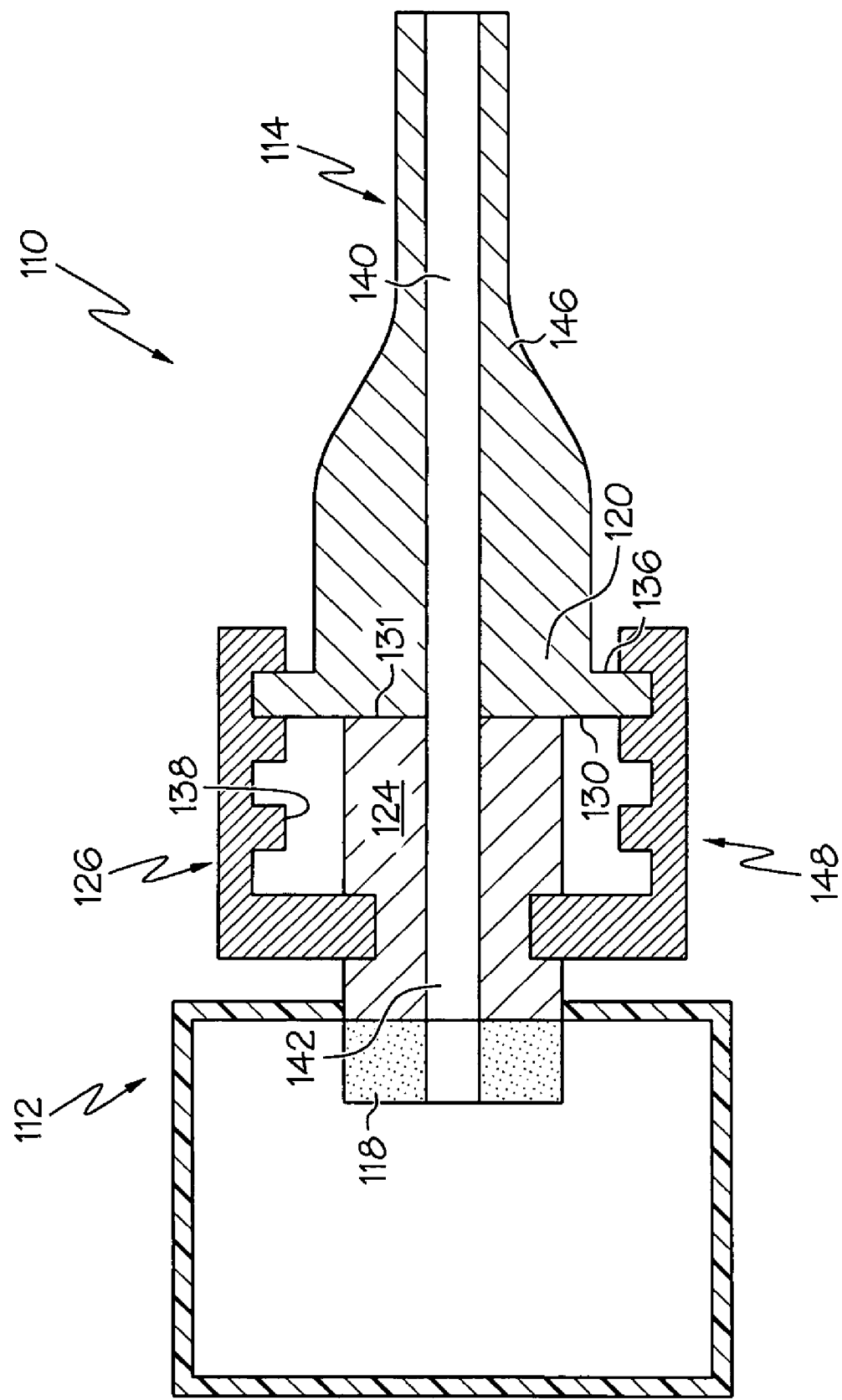
FIG. 2 is a schematic cross-sectional view of a second embodiment of an ultrasonic medical instrument of the invention, including an embodiment of a medical-instrument connection assembly of the invention, wherein the handpiece makes a non-tapered physical contact with the end effector portion of the blade, and wherein the third connecting member is rotatably attached to the second connecting member.

In a second application, as shown in the embodiment of the handpiece and medical ultrasonic blade assembly 110 of FIG. 2, the first connecting member 120 includes a substantially longitudinally-facing flat surface 130, and the second connecting member 124 has a substantially longitudinally-facing flat surface 131 abuttingly engaging the substantially longitudinally-facing flat surface 130 of the first connecting member 120. In one variation, the first connecting member 120 has a substantially transversely-outwardly-extending annular wing 136, and the third connecting member 126 has internal threads 138 threadably engaging the annular wing 136. In one modification, the first connecting member 120 has a first lumen 140, and the second connecting member 124 has a second lumen 142 in fluid communication with the first lumen 140.

In one configuration of the first expression of the embodiment of FIG. 1, the medical ultrasonic blade 14 includes a proximal wave guide portion 44 and a distal end effector portion 46, and the proximal wave guide portion 44 is threadably engaged by the handpiece 12. In a second configuration, as shown in the second embodiment of FIG. 2, the medical ultrasonic blade 114 includes an end effector portion 146, and the end effector portion 146 is threadably engaged by the handpiece 112. In one variation, the handpiece 112 includes an ultrasound transducer 118.

A second expression of the embodiment of FIG. 1 is for a medical-instrument connection assembly 48 for transmitting ultrasonic vibrations and includes an ultrasound-medical-instrument first connecting member 20, an ultrasound-medical-instrument second connecting member 24, and an ultrasound-medical-instrument third connecting member 26. The first connecting member 20 is adapted to be ultrasonically vibrated and has a longitudinal axis 22. The second connecting member 24 is disposable to be substantially coaxially aligned with the longitudinal axis 22 and in contact with the first connecting member 20. The third connecting member 26 surrounds, and is rotatably or fixedly attached to, the second connecting member 24 and is threadably engageable with the first connecting member 20. In one example, one or more of the connecting members 20, 24 and 26 is operatively connected to, or a monolithic portion of, a medical ultrasonic blade 14, and in another example, not shown, there is no medical ultrasonic blade present.

In a first employment of the second expression of the embodiment of FIG. 1, a medical ultrasonic blade 14, of a handpiece and medical ultrasonic blade assembly 10 of an ultrasonic medical instrument 8, includes the first connecting member 20, and a handpiece 12, of the handpiece and medical ultrasonic blade assembly 10, includes the second and third connecting members 24 and 26. In a second employment, not shown, a handpiece, of a handpiece and medical ultrasonic blade assembly of an ultrasonic medical instrument, includes the first connecting member, and a medical ultrasonic blade, of the handpiece and medical ultrasonic blade assembly, includes the second and third connecting members.

In a first application of the second expression of the embodiment of FIG. 1, the first connecting member 20 includes a substantially longitudinally-facing surface 30 having a tapered recess 32, and the second connecting member 24 has a tapered end 34 engaged in the tapered recess 32. The taper of the tapered recess 32 is greater than the taper of the tapered end 34 to insure ultrasound-transmitting physical contact. In one variation, the first connecting member 20 has a substantially transversely-outwardly-extending annular wing 36, and the third connecting member 26 has internal threads 38 threadably engaging the annular wing 36. In one modification, the first connecting member 20 has a first lumen 40, and the second connecting member 24 has a second lumen 42 in fluid communication with the first lumen 40. In one example, the first, second and third connecting members 20, 24 and 26 together define a luer-type connection.

In a second application, as shown in the embodiment of the medical-instrument connection assembly 148 of FIG. 2, the first connecting member 120 includes a substantially longitudinally-facing flat surface 130, and the second connecting member 124 has a substantially longitudinally-facing flat surface 131 abuttingly engaging the substantially longitudinally-facing flat surface 130 of the first connecting member 120. In one variation, the first connecting member 120 has a substantially transversely-outwardly-extending annular wing 136, and the third connecting member 126 has internal threads 138 threadably engaging the annular wing 136. In one modification, the first connecting member 120 has a first lumen 140, and the second connecting member 124 has a second lumen 142 in fluid communication with the first lumen 140.

Several benefits and advantages are obtained from one or more of the expressions of an embodiment of the invention. In one example, physical contact and threadable engagement (internal threads on the handpiece acting on the external diameter of the blade) proximate a longitudinal vibration antinode provide improved ultrasound transfer while threadable engagement radially apart from the physical contact allows for a quick connection (and disconnection) without requiring multiple turns or a torque limiting device while reducing the possibility of stripped or broken threads.

While the present invention has been illustrated by a description of several embodiments, it is not the intention of the applicants to restrict or limit the spirit and scope of the appended claims to such detail. Numerous other variations, changes, and substitutions will occur to those skilled in the art without departing from the scope of the invention. For instance, the ultrasonic medical instrument and the medical-instrument connection assembly of the invention have application in robotic assisted surgery taking into account the obvious modifications of such systems, components and methods to be compatible with such a robotic system. It will be understood that the foregoing description is provided by way of example, and that other modifications may occur to those skilled in the art without departing from the scope and spirit of the appended Claims.

What is claimed is:

1. An ultrasonic medical instrument comprising a handpiece and medical ultrasonic blade assembly, wherein the handpiece and medical ultrasonic blade assembly includes:
   a) a vibration antinode;
   b) a handpiece; and
   c) a medical ultrasonic blade, wherein the medical ultrasonic blade includes a first connecting member having a longitudinal axis, wherein the handpiece includes a second connecting member which is substantially coaxially aligned with the longitudinal axis and which has a distal portion which is in non-threadable and ultrasound-transmitting direct physical contact with a proximal portion of the first connecting member proximate the vibration antinode, wherein the handpiece includes a third connecting member which surrounds and is rotatably or fixedly attached to the second connecting member and which is threadably engaged with the first connecting member proximate the vibration antinode, and wherein the third connecting member is attached to the second connecting member when the medical ultrasonic blade is attached to the handpiece and the medical ultrasonic blade can be completely removed from the handpiece without removing the third connecting member from the second connecting member.

2. The ultrasonic medical instrument of claim 1, wherein the first connecting member is a monolithic portion of the medical ultrasonic blade, wherein the handpiece includes an ultrasound transducer and a protrusion operatively connected to the ultrasound transducer, and wherein the second connecting member is a monolithic portion of the protrusion.

3. The ultrasonic medical instrument of claim 1, wherein the first connecting member includes a substantially longitudinally-facing surface having a tapered recess, and wherein the second connecting member has a tapered end engaged in the tapered recess.

4. The ultrasonic medical instrument of claim 3, wherein the first connecting member has a substantially transversely-outwardly-extending annular wing, and wherein the third connecting member has internal threads threadably engaging the annular wing.

5. The ultrasonic medical instrument of claim 4, wherein the first connecting member has a first lumen, and wherein the second connecting member has a second lumen in fluid communication with the first lumen.

6. The ultrasonic medical instrument of claim 5, wherein the first, second and third connecting members together define a luer-type connection.

7. The ultrasonic medical instrument of claim 1, wherein the first connecting member includes a substantially longitudinally-facing transverse flat surface, wherein the second connecting member has a substantially longitudinally-facing transverse flat surface abuttingly engaging the substantially longitudinally-facing transverse flat surface of the first connecting member, and wherein the second connecting member does not engage any other surface of the first connecting member.

8. The ultrasonic medical instrument of claim 7, wherein the first connecting member has a substantially transversely-outwardly-extending annular wing, and wherein the third connecting member has internal threads threadably engaging the annular wing.

9. The ultrasonic medical instrument of claim 8, wherein the first connecting member has a first lumen, and wherein the second connecting member has a second lumen in fluid communication with the first lumen.

10. The ultrasonic medical instrument of claim 1, wherein the medical ultrasonic blade includes an end effector portion, and wherein the end effector portion is threadably engaged by the handpiece.

11. The ultrasonic medical instrument of claim 1, wherein the medical ultrasonic blade includes a proximal wave guide portion and a distal end effector portion, and wherein the proximal wave guide portion is threadably engaged by the handpiece.

12. The ultrasonic medical instrument of claim 1, wherein the second connecting member is in non-threadable and ultrasound-transmitting direct physical contact with a proximal portion of the first connecting member at a vibration antinode.

* * * * *